US011872093B1

(12) United States Patent
Bawaadam et al.

(10) Patent No.: US 11,872,093 B1
(45) Date of Patent: Jan. 16, 2024

(54) METHOD OF MARKING LESIONS

(71) Applicants: Hasnain S. Bawaadam, Vernon Hills, IL (US); Ganesh Krishna, Saratoga, CA (US)

(72) Inventors: Hasnain S. Bawaadam, Vernon Hills, IL (US); Ganesh Krishna, Saratoga, CA (US)

(73) Assignee: NoduGloH LLC, Vernon Hills, IL (US)

( * ) Notice: Subject to any disclaimer, the term of this patent is extended or adjusted under 35 U.S.C. 154(b) by 0 days.

(21) Appl. No.: 18/173,891

(22) Filed: Feb. 24, 2023

Related U.S. Application Data

(60) Provisional application No. 63/478,994, filed on Jan. 9, 2023, provisional application No. 63/369,228, filed on Jul. 23, 2022, provisional application No. 63/369,129, filed on Jul. 22, 2022.

(51) Int. Cl.
*A61B 90/00* (2016.01)
*A61K 49/00* (2006.01)

(52) U.S. Cl.
CPC .......... *A61B 90/39* (2016.02); *A61K 49/0034* (2013.01); *A61B 2090/3908* (2016.02); *A61B 2090/3962* (2016.02); *A61B 2090/3966* (2016.02); *A61B 2090/3983* (2016.02); *A61B 2090/3987* (2016.02)

(58) Field of Classification Search
CPC . A61B 90/39; A61B 34/20; A61B 2090/3908; A61K 49/003
See application file for complete search history.

(56) References Cited

U.S. PATENT DOCUMENTS

2006/0009785 A1* 1/2006 Maitland .............. A61B 17/221
606/113

OTHER PUBLICATIONS

Baker et al. Endovascular Coils as Lung Tumor Fiducial Markers for Real-Time Tumor Tracking in Stereotactic Body Radiotherapy: Comparison of Complication Rates with Transthoracic Fiducial Marker Placement. J Vasc Interv Radiol, 2019; 30:1901-1907. https://doi.org/10.1016/j.jvir.2019.04.025. (Year: 2019).*
YouTube video clip entitled "Placement of Coil Spring Fiducial Markers Using Ion Robotic Bronchoscopy", uploaded May 9, 2022 by Robotic Bronchoscopy by AB. Alraiyes: https://www.youtube.com/watch?v=5wCUHQmNBXM. (Year: 2022).*

(Continued)

*Primary Examiner* — Angela M Hoffa
*Assistant Examiner* — Younhee Choi
(74) *Attorney, Agent, or Firm* — Umair A. Qadeer

(57) ABSTRACT

A method of marking lesions is disclosed herein. The disclosed method may assist surgeons localize small nodules by marking the nodules with a fiducial coil soaked with a fluorescent dye. In some preferred embodiments, the fiducial coil is placed at the time of biopsy using a robotic surgery system. In alternate embodiments, non-robotic peripheral navigation platforms may also be used effectively as an adjunct to surgical resection. The dye marks the location of a nodule, making it visible and palpable at the time of surgery. A surgeon may then target cancerous tissue with greater precision. The disclosed method allows a fiducial coil to be placed several days prior to surgery.

20 Claims, 2 Drawing Sheets

(56) References Cited

OTHER PUBLICATIONS

Schroeder et al. Coil spring fiducial markers placed safely using navigation bronchoscopy in inoperable patients allows accurate delivery of CyberKnife sterotactic radiosurgery. The Journal of Thoracic and Cardiovascular Surgery, 2010; 120: 1137-1142. https://doi.org/10.1016/j.jtcvs.2010.07.085. (Year: 2010).*

YouTube video clip entitled "Fiducial Markers Placement Using REBUS and ION robotic bronchoscopy Fluoroscopy Reference Function", uploaded Feb. 5, 2022 by Robotic Bronchoscopy by AB. Alraiyes: https://www.youtube.com/watch?v=8ZcHAzzsYys. (Year: 2022).*

Anantham et al. Electromagnetic Navigation Bronchoscopy-Guided Fiducial Placement for Robotic Stereotactic Radiosurgery of Lung Tumors. Chest, 2007; 132: 930-935. https://doi.org/10.1378/chest.07-0522. (Year: 2007).*

Kong et al. Robust augmented reality registration method for localization of solid organs' tumors using CT-derived virtual biomechanical model and fluorescent fiducials. Surg Endosc 31, 2863-2871 (2017). https://doi.org/10.1007/s00464-016-5297-8. (Year: 2017).*

Chan et al. Electromagnetic navigation bronchoscopy fiducial marker margin identification plus triple dye for complete lung nodule resection. JTCVS Tech. Jul. 11, 2020;3:329-333. doi: 10.1016/j.xjtc.2020.07.010.) (Year: 2020).*

Ward et al. Identifying lost surgical needles with visible and near infrared fluorescent light emitting microscale coating, Surgery, vol. 163, Issue 4, 2018, pp. 883-888, https://doi.org/10.1016/j.surg.2017.10.025. (Year: 2018).*

Bawaadam, et al. "Lung Nodule Marking With ICG Dye-Soaked Coil Facilitates Localization and Delayed Surgical Resection," Ann. Thorac. Surg. Short Reports, 2023, 1, 221-25. DOI: 10.1016/j.atssr.2023.02.010. (Year: 2023).*

Krisha, G. "Interventional Pulmonology: Role in Lung Cancer Management," Cal. Thoracic Society, 2018, available at: https://calthoracic.org/2018-presentations/.

Anantham, D., et al. "Electromagnetic navigation bronchoscopy-guided fiducial placement for robotic stereotactic radiosurgery of lung tumors: a feasibility study," Chest, 2007, 132(3), 930-5, doi: 10.1378/chest.07-0522.

Anayama, T., et al. "Localization of pulmonary nodules using navigation bronchoscope and a near-infrared fluorescence thoracoscope," Ann. Thorac. Surg. 2015, 99(1), 224-30, doi: 10.1016/j.athoracsur.2014.07.050.

Anayama, T., et al. "Near-infrared dye marking for thoracoscopic resection of small-sized pulmonary nodules: comparison of percutaneous and bronchoscopic injection techniques," J. Cardiothorac. Surg. 2018, 13(1), 5, doi: 10.1186/s13019-018-0697-6.

Bolton, W.D., et al. "The utility of electromagnetic navigational bronchoscopy as a localization tool for robotic resection of small pulmonary nodules," Ann. Thorac. Surg. 2014, 98(2), 471-5, doi: 10.1016/j.athoracsur.2014.04.085.

Chan, J.W.Y., et al. "Robotic Assisted-Bronchoscopy With Cone-Beam CT ICG Dye Marking for Lung Nodule Localization: Experience Beyond USA," Front. Surg. 2022, 9, 943531, doi: 10.3389/fsurg.2022.943531.

Chen, S., et al. "Video-assisted thoracoscopic solitary pulmonary nodule resection after CT-guided hookwire localization: 43 cases report and literature review," Surg. Endosc. 2011, 25(6), 1723-9, doi: 10.1007/s00464-010-1502-3.

Ferrari-Light, D., et al. "The Utility of Near-Infrared Fluorescence and Indocyanine Green During Robotic Pulmonary Resection," Front. Surg. 2019, 6, 47, doi: 10.3389/fsurg.2019.00047.

Finley, R.J., et al. "Preoperative computed tomography-guided microcoil localization of small peripheral pulmonary nodules: a prospective randomized controlled trial," J. Thorac. Cardiovasc. Surg. 2015, 149(1), 26-31, doi: 10.1016/j.jtcvs.2014.08.055.

Gkikas, A., et al. "How effective is indocyanine green (ICG) in localization of malignant pulmonary nodules? A systematic review and meta-analysis," Front. Surg. 2022, 9, 967897, doi: 10.3389/fsurg.2022.967897.

Krishna, G. "Interventional Pulmonology: Role in Lung Cancer Management," Cal. Thoracic Society, 2018, available at: https://calthoracic.org/2018-presentations/.

Lenglinger, F.X., et al. "Localization of pulmonary nodules before thoracoscopic surgery: value of percutaneous staining with methylene blue," AJR Am. J. Roentgenol. 1994, 163(2), 297-300, doi: 10.2214/ajr.163.2.7518642.

Lin, M.W., et al. "Computed tomography-guided patent blue vital dye localization of pulmonary nodules in uniportal thoracoscopy," J. Thorac. Cardiovasc. Surg. 2016, 152(2), 535-544.e2, doi: 10.1016/j.jtcvs.2016.04.052.

Mayo, J.R., et al. "Lung nodules: CT-guided placement of microcoils to direct video-assisted thoracoscopic surgical resection," Radiology, 2009, 250(2), 576-85, doi: 10.1148/radiol.2502080442.

McConnell, P.I., et al. "Methylene blue-stained autologous blood for needle localization and thoracoscopic resection of deep pulmonary nodules," J. Pediatr. Surg. 2002, 37(12), 1729-31, doi: 10.1053/jpsu.2002.36707.

McDermott, S., et al. "Preoperative CT-guided Fiducial Marker Placement for Surgical Localization of Pulmonary Nodules," Radiol. Cardiothorac. Imaging, 2022, 4(1), e210194, doi: 10.1148/ryct.210194.

Miyoshi, T., et al. "Fluoroscopy-assisted thoracoscopic resection of pulmonary nodules after computed tomography—guided bronchoscopic metallic coil marking," J. Thorac. Cardiovasc. Surg. 2006, 131(3), 704-10, doi: 10.1016/j.jtcvs.2005.09.019.

Moon, S.W., et al. "Fluoroscopy-aided thoracoscopic resection of pulmonary nodule localized with contrast media," Ann. Thorac. Surg. 1999, 68(5), 1815-20, doi: 10.1016/s0003-4975(99)00764-x.

Powell, T.I., et al. Peripheral Lung Nodules: Fluoroscopically Guided Video-Assisted Thoracoscopic Resection After Computed Tomography-Guided Localization Using Platinum Microcoils, Ann. Surg. 2004, 240(3), 481-8, doi: 10.1097/01.sla.0000137132.01881.57.

Rodrigues, J.C.L., et al. "CT-guided Microcoil Pulmonary Nodule Localization prior to Video-assisted Thoracoscopic Surgery: Diagnostic Utility and Recurrence-Free Survival," Radiology, 2019, 291(1), 214-22, doi: 10.1148/radiol.2019181674.

Schroeder, C., et al. "Coil spring fiducial markers placed safely using navigation bronchoscopy in inoperable patients allows accurate delivery of CyberKnife stereotactic radiosurgery," J. Thorac. Cardiovasc. Surg. 2010, 140(5), 1137-42 doi: 10.1016/j.jtcvs.2010.07.085.

Ujiie, H., et al. "A novel minimally invasive near-infrared thoracoscopic localization technique of small pulmonary nodules: A phase I feasibility trial," J. Thorac. Cardiovasc. Surg. 2017, 154(2), 702-11, doi: 10.1016/j.jtcvs.2017.03.140.

Wang, L., et al. "Computed tomography-guided localization of pulmonary nodules prior to thoracoscopic surgery," Thorac. Cancer, 2023, 14(2), 119-26, doi: 10.1111/1759-7714.14754.

Wu, Z., et al. "Localization of subcentimeter pulmonary nodules using an indocyanine green near-infrared imaging system during uniportal video-assisted thoracoscopic surgery," J. Cardiothorac. Surg. 2021, 16(1), 224, doi: 10.1186/s13019-021-01603-x.

Yanagiya, M., et al. "Initial experience of virtual-assisted lung mapping utilizing both indocyanine green and indigo carmine," Gen. Thorac. Cardiovasc. Surg. 2021, 69, 1035-39, doi: 10.1007/s11748-020-01565-2.

Yang, Y.L., et al. "Electromagnetic navigation bronchoscopic localization versus percutaneous CT-guided localization for thoracoscopic resection of small pulmonary nodules," Thorac. Cancer, 2021, 12(4), 468-74, doi: 10.1111/1759-7714.13775.

* cited by examiner

FIG. 3
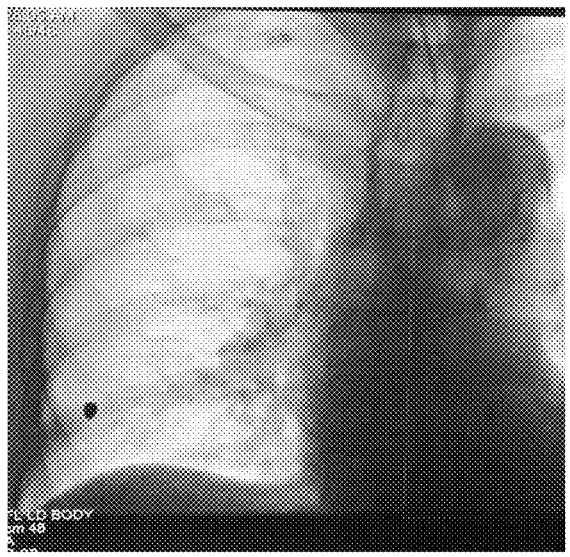
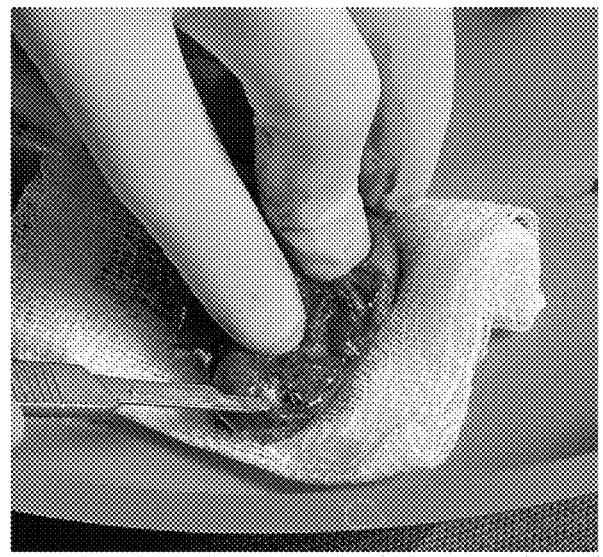
FIG. 4A
FIG. 4B

METHOD OF MARKING LESIONS

CROSS-REFERENCE TO RELATED APPLICATIONS

This application claims the benefit of U.S. Provisional Patent Application Ser. No. 63/478,994, filed on Jan. 9, 2023; 63/369,228, filed on Jul. 23, 2022; and 63/369,129, filed on Jul. 22, 2022; the disclosures of which are hereby incorporated herein in their entireties by reference.

BACKGROUND

Pulmonary nodules are now more readily identified with the increased use of computed tomography (CT) of the chest and lung cancer screening efforts. The percentage of early-stage lung cancer has also increased. While surgical resection for this stage is the standard of care, an increasing interest in and literature supporting lung sparing surgery, both for new lung cancers and secondary metastasis to the lung, requires precise localization techniques to provide optimal outcomes. Ideal localization procedures will offer multiple options for surgeons to clearly identify these nodules and to allow the best chance to preserve as much healthy lung tissue as possible.

Surgical localization of lung nodules, however, may present multiple challenges. Several tumor factors, including the size of the nodule, the distance from the pleural surface, the nature of the nodule (ground glass, solid, or mixed), and factors such as associated structural lung disease, the presence of anthracotic pigment on the lung surface, and pleural adhesions have important implications in localization and surgical resection. Other potential barriers include access to the procedure/proceduralist, logistical challenges within institutions, and reliance upon open surgical techniques.

While diagnosis and treatment of pulmonary nodules may be combined during a surgical resection, this approach may lead to excision of benign lesions and excessive healthy lung tissue if the lesion is difficult to localize. Bronchoscopic guided marking of pulmonary nodules prior to surgery may facilitate this process, but it is limited by current technologies and often challenging as dye marking may dissipate if surgery is performed days later.

With increasing interest in lung sparing surgery, both for de novo lung cancers and secondary metastasis to the lung, precise localizations are now more important for providing desirable outcomes. Ideal localization procedures will offer multiple options for surgeons to precisely identify lung nodules.

Thus, there remains a need for a method of accurate marking of lesions for precise identification of lung nodules after a clinically significant period of time.

SUMMARY

The present disclosure describes a novel method for addressing the problem of surgical localization of lung nodules and adds efficiency between a diagnosis and subsequent surgery. The disclosed method may assist surgeons localize small nodules by marking the nodules with a fiducial coil soaked with Indocyanine Green (ICG) dye. In some preferred embodiments, the fiducial coil is placed at the time of biopsy using a robotic bronchoscopy system. In alternate embodiments, non-robotic peripheral navigation platforms may also be used effectively as an adjunct to surgical resection. The dye marks the location of the lung nodule, making it visible and palpable at the time of surgery. The surgeon can then target the cancer tissue with greater precision, allowing for lung sparing surgery. The disclosed method allows a fiducial coil to be placed several days prior to surgery.

Although the description above describes a method of marking lesions in the lungs, the disclosed method may be used to mark lesions in other tissues and organs in the body.

In addition, although the description above describes a method of marking lesions using a specific coil, it is contemplated that any biocompatible coil suitable for use in the human body, including coils composed of biocompatible metals or alloys, biocompatible polymers, or other biocompatible materials, may be used in the disclosed method.

Further, although the description above describes the use of a specific biocompatible fluorescent dye, it is contemplated that any biocompatible fluorescent dye suitable for use in the human body may be used in the disclosed method.

Also, although the description above describes a procedure of soaking the coil in the dye shortly before placing the dye-soaked coil as a marker, it is contemplated that the coil may alternatively be pre-soaked in an appropriate amount of a fluorescent dye and the pre-soaked coil is used in the disclosed method. The shelf-life of pre-soaked coils will depend on the specific dye and the material of which the coil is composed.

Finally, although the description above describes the use of a coil that is completely soaked in the dye, it is also contemplated that only a portion of the coil is soaked in the dye and such a partially soaked coil is used in the disclosed method.

BRIEF DESCRIPTION OF THE DRAWINGS

FIG. 2A shows a cross-sectional CT image with a fiducial marker placed in an right upper lobe with a ground glass lesion, and FIG. 2B shows a cross-sectional CT image with a fiducial marker placed in an right upper lobe with a solid nodule.

FIG. 3 shows a visualization of an embodiment of a dye-soaked coil as a fluorescent target on the pleural surface.

FIG. 4A shows a view of an embodiment of a robotic lung wedge resection being successfully performed using luminescence provided by the dye-soaked coil.

FIG. 4B shows an embodiment of a resected wedge showing a fiducial coil in the middle of the specimen.

DETAILED DESCRIPTION

Figure 1:
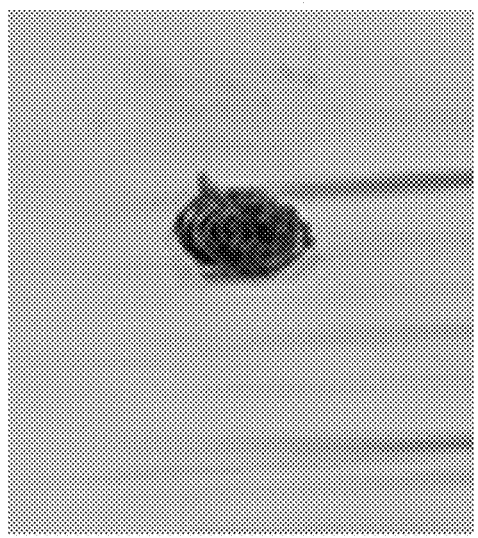
FIG. 1 illustrates an embodiment of the dye-soaked coil used in the disclosed method.

The present disclosure describes a novel method for addressing the problem of surgical localization of lung nodules and adds efficiency between a diagnosis and subsequent surgery. The disclosed method may assist surgeons localize small nodules by marking the nodules with a fiducial coil soaked with Indocyanine Green (ICG) dye. In some preferred embodiments, the fiducial coil is placed at the time of biopsy using a robotic bronchoscopy system. In alternate embodiments, non-robotic peripheral navigation platforms may also be used effectively as an adjunct to surgical resection. The dye marks the location of the lung nodule, making it visible and palpable at the time of surgery. The surgeon can then target the cancer tissue with greater precision, allowing for lung sparing surgery.

The disclosed method allows a fiducial coil to be placed several days prior to surgery.

In exemplary studies conducted at multiple locations, ICG-dye soaked coils were placed in biopsy-proven cancerous lung nodules of patients preparing for surgery several days later, where the coil placement was performed 0-9 days before surgery. Since the coils were carrying the dye, the fluorescent and bright-neon green was still visible even after at least five days. The bright green luminescence of the dye enabled the respective thoracic surgeons to know exactly where to resect, minimizing the amount of lung tissue removed and resulting in a better outcome for the patients. The coil is also palpable and visible by intra-operative fluoroscopy or ultrasound, allowing the surgeon multiple options to localize the lesion, depending on experience and expertise. Where available, imaging technologies such as cone beam CT or augmented fluoroscopy images may also be used to assist with assessing the position of the coil in relationship to the nodule, thereby aiding in precise resection.

The extended time allowed between use of the disclosed method to place a marker and the subsequent surgery provides substantial advantages for patients at smaller, rural peripheral hospitals with limited availability for on-site thoracic surgery. Patients may need time to schedule, prepare, and travel to larger medical centers for surgery. The disclosed method of fiducial marking means patients will arrive at the surgery center for a surgical procedure that will allow appropriate localization and visualization to aid resection by the surgeon.

The disclosed method benefits patients by providing surgeons with a more efficient, faster, and precise surgical method that better preserves healthy tissue. This disclosed method will substantially improve the trajectory of successful lung sparing surgery for both primary and secondary malignancies of the lungs.

Although the description above describes a method of marking lesions in the lungs, the disclosed method may be used to mark lesions in other tissues and organs in the body.

In addition, although the description above describes a method of marking lesions using a specific coil, it is contemplated that any biocompatible coil suitable for use in the human body, including coils composed of biocompatible metals or alloys, biocompatible polymers, or other biocompatible materials, may be used in the disclosed method.

Further, although the description above describes the use of a specific biocompatible fluorescent dye, it is contemplated that any biocompatible fluorescent dye suitable for use in the human body may be used in the disclosed method.

Also, although the description above describes a procedure of soaking the coil in the dye shortly before placing the dye-soaked coil as a marker, it is contemplated that the coil may alternatively be pre-soaked in an appropriate amount of a fluorescent dye and the pre-soaked coil is used in the disclosed method. The shelf-life of pre-soaked coils will depend on the specific dye and the material of which the coil is composed.

Finally, although the description above describes the use of a coil that is completely soaked in the dye, it is also contemplated that only a portion of the coil is soaked in the dye and such a partially soaked coil is used in the disclosed method.

EXAMPLES

The following examples are provided as specific illustrations of the disclosed method. It should be understood, however, that the invention is not limited to the specific details set forth in the examples.

Further, any range of numbers recited above or in the paragraphs hereinafter describing or claiming various aspects of the invention, such as ranges that represent a particular set of properties, units of measure, conditions, physical states, or percentages, is intended to literally incorporate, expressly herein by reference or otherwise, any number falling within such range, including any subset of numbers or ranges subsumed within any range so recited. The term "about" when used as a modifier for or in conjunction with a variable, is intended to convey that the numbers and ranges disclosed herein may be flexible as understood by ordinarily skilled artisans and that practice of the disclosed invention by those skilled in the art using temperatures, concentrations, amounts, contents, and properties that are outside of a literal range will achieve the desired result.

Case Studies

The following case studies illustrate the disclosed method.

Materials and Methods

One patient at El Camino Hospital/Palo Alto Medical Foundation in Mountain View, CA and three patients at Aurora Medical Center in Kenosha, Kenosha, WI with incidentally detected lung nodules were selected for proof-of-concept studies of the disclosed method. The selection was based on the scheduled time between the marking procedure and thoracic surgery (0, 4, 5 and 9 days between ICG dye-soaked coil placement and surgical resection).

Materials used in the procedures were a fiducial coil (G10417 Tornado Embolization Coil 7 mm×3 mm×0.035 in ×8 cm, Cook Medical, Bloomington, IN, USA) soaked with indocyanine green dye (ICG) (NDC-70100-424-02, HUB Pharmaceuticals, Scottsdale, AZ, USA) for 10 minutes prior to placement by robotic bronchoscopy using the Ion Endoluminal System (Intuitive Surgical, Sunnyvale, CA, USA) 0-9 days prior to thoracic surgery.

All patients underwent robotic assisted navigation bronchoscopy (RANB) using the Ion Endoluminal System (Intuitive Surgical, Sunnyvale, CA, USA) with either cone beam computed tomography or 3D fluoroscopy used for secondary confirmation as an additional tool. The fixed ceiling mounted Artis Zee cone beam scanner (Siemens Medical Solutions, Malvern, PA, USA) was used at El Camino Hospital (n=1) whereas the mobile C-arm Cios Spin (Siemens Medical Solutions, Malvern, PA, USA) was used at the Aurora Medical Center in Kenosha (n=3). All patients presented with new, incidentally detected nodules (two with solid nodules and two with a ground-glass opacities). None of the patients had a history of allergic reaction to contrast dyes. The procedures were planned as diagnostic bronchoscopies with biopsy followed by marking (if intra-procedural cytopathology showed atypical cells or confirmed malignancy) and subsequent surgical resection (planned for a later date at the Kenosha, WI facility and same day at the Mountain View, CA location).

The procedures were performed by marking the lesions with ICG dye-soaked Cook Tornado Coils, as shown in FIG. 1, using the robotic assisted navigation bronchoscopy method. Using a standard 1 ml tuberculin syringe with a luer lock, 0.25 ml of a pre-diluted mixture of ICG (25 mg of ICG dye mixed with 10 ml of sterile water resulting in a 2.5 mg/ml ICG dye concentration) was drawn and injected into the Cook Tornado coil cartridge sheath, priming the sheath, and soaking the coil within it with the ICG dye. The dwell time for the dye to soak the coil completely was 10 minutes.

This amount of time was selected to allow adequate soaking of the synthetic fibers of the coil. After the dwell time elapsed, another 0.25 ml of the same mixture of ICG dye was instilled within the coil sheath for additional priming just prior to ICG dye-soaked coil placement within the targeted nodule. The ICG impregnated coil was then back-loaded into the superDimension delivery catheter and was deployed by pushing the guidewire that is included with the catheter kit (superDimension™ Marker Delivery Kit, Medtronic, MN, USA).

Figure 2A:
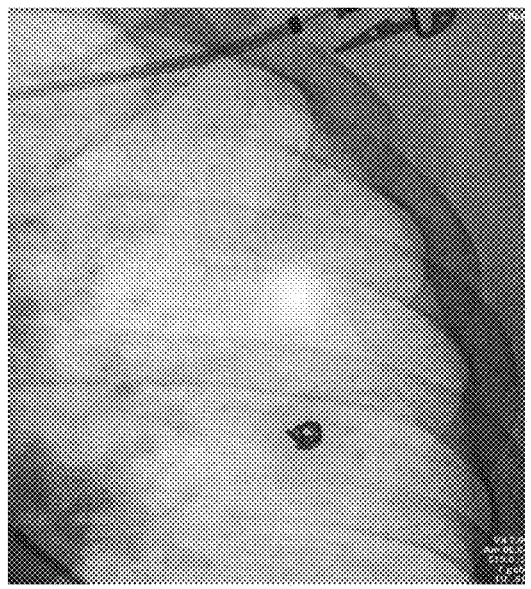
FIGS. 2A-2B show embodiments of the dye-soaked coil delivered via the robotic catheter at the nodule site, where
Figure 2B:
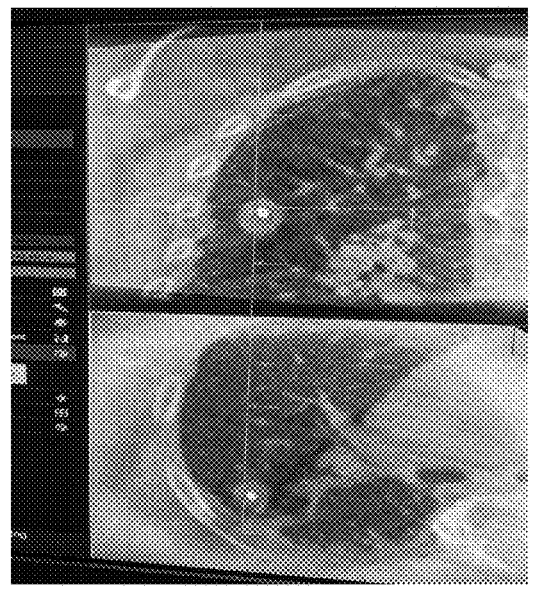

Once the ICG soaked coil was deployed within the target lesion, as shown in FIG. 2, one patient was then directly transported to the operating room for robotic wedge resection (da Vinci, Intuitive Surgical, Sunnyvale, CA, USA) on the same day as a single anesthetic procedure in Mountain View and three patients from Kenosha were transported to the recovery room and then discharged home. These patients underwent robotic thoracic surgery 4, 5, and 9 days later, respectively, at another Aurora Medical Center facility where thoracic surgery services were available.

Results

Four patients underwent the procedure described in the embodiments of the disclosed method that are described herein. All lesions were <2 cm on pre-procedure chest CT (two ground glass nodules, sized 12 mm and 15 mm, and two solid nodules, sized 10 mm and 15 mm), located in the outer third of the lung, and without a bronchus sign.

ICG dye-soaked coils were placed in biopsy-proven cancerous lung nodules of patients preparing for surgery both immediately after the procedure (day 0) as well as several days later (days 4, 5, and 9). Successful nodule localization was achieved for all nodules with visualization of the dye-soaked coil as a neon-green target on the pleural surface, as shown in FIG. 3, using the Firefly Fluorescence Imaging system (da Vinci Fluorescence Imaging Vision System, da Vinci, Intuitive Surgical, Sunnyvale, CA, USA) of the da Vinci robotic system (da Vinci, Intuitive Surgical, Sunnyvale, CA, USA). Wedge resection with negative margins was successfully performed on all four cases using the neon-green luminescence provided by the dye-soaked coil with accurate localization and resection, as shown in FIGS. 4A-4B. Patients that met criteria for further anatomical lung resection based on frozen pathology results of the wedge resection then received further resection during that anesthetic episode. No periprocedural or postoperative complications were identified. Because the coil is made with platinum and spaced synthetic fibers, the ICG dye adheres to the coil, allowing the fluorescent and bright-neon green to still be visible even after at least nine days. The bright green dye luminescence enabled the thoracic surgeons to know exactly where to resect, potentially decreasing the amount of lung tissue removed. Previously, localizing a nodule nine days after ICG dye marking without use of a coil was not possible, as the dye effect would fade away over several hours due to its metabolism and half-life. The ICG dye-soaked coil marks the nodule location, making it visible under the Firefly Fluorescence Imaging system of the da Vinci robotic system that allows the surgeon to target the lesion with greater precision, allowing for a lung sparing surgery. The coil is also palpable by surgical graspers and visible by intra-operative fluoroscopy or ultrasound, allowing the surgeon multiple options using the chemical and mechanical properties of a dye impregnated coil to localize the lesion, depending on experience and expertise.

Analysis of Exemplary Procedures

Nodule localization facilitates surgical resection and prevents excision of benign disease and healthy lung tissue. Successful localization lacks a clear definition, however, and is usually subjectively assessed by the proceduralist. Failure may occur if the surgeon is unable to clearly visualize or palpate the lesion, leading to increased procedural time and healthy lung tissue resected, changes in the operative approach, and possible failure to remove the intended target. Failure to detect pulmonary nodules greater than 5 mm from the pleural surface and less than 10 mm in size is greater than 60% during a video-assisted thoracoscopic approach. Additionally, pure ground glass lesions are challenging to palpate. In the disclosed exemplary patients, all lesions were <15 mm, located in the outer third of the lung, and without a bronchus sign. Two lesions were solid and two were ground glass. All were localized during surgery up to 9 days after marking without seeing any dye dispersion.

A fiducial coil soaked with ICG was used because these coils are made with platinum and spaced synthetic fibers, which allows the ICG dye to adhere thereto. The shape of the deployed coil with a broad base and progressively narrowing coils is well suited for deployment in the small airways or lung parenchyma. The deployed coil is also easy to feel with fingers or graspers. The deployed shape of the dye impregnated coil is well visualized by fluroscopy, ultrasound, or illumination methods. It was contemplated that this construction would allow the fluorescent and bright-neon green dye to still be visible many days later, which was seen in exemplary patients after at least nine days. The bright green dye luminescence enabled the thoracic surgeons to know exactly where to resect, potentially decreasing the amount of lung tissue removed. Prior to this, localizing a nodule nine days after ICG dye marking without a coil was not possible, as the dye effect would fade away over several hours due to its metabolism and half-life. The ICG dye-soaked coil marks the nodule location, making it visible under the Firefly Fluorescence Imaging system of the da Vinci robotic system that allows the surgeon to target the lesion with greater precision, allowing for a lung sparing surgery. The coil is also palpable by surgical graspers and visible by intra-operative fluoroscopy or ultrasound, allowing the surgeon multiple options using the chemical and mechanical properties of a dye impregnated coil to localize the lesion, depending on experience and expertise.

It is hypothesized that dye retention after multiple days is based on the interaction of the ICG dye with the synthetic fibers of the coil. While ICG has a short half-life when injected and is subject to non-specific protein binding and poor photostability, these limitations may be overcome through conjugation of ICG with other substances, such as lipids, metals, or nanoparticles. As a result, it was contemplated that binding ICG to the synthetic fibers of the coil would allow for retention of the beneficial properties of ICG, namely enhanced visualization, while mitigating these limitations.

Although the dye-soaked coils were placed in biopsy confirmed or suspected malignant lesions with the exemplary patients, the disclosed method may also be used for non-diagnostic lesions with high suspicion and planned surgical biopsy or resection. The extended time allowed before surgery with this ICG-fiducial marker method may provide substantial advantages for patients at smaller rural or underserved hospitals with poor access to or limited availability for on-site thoracic surgery. Similarly, larger academic centers, where a single anesthetic procedure with localization followed by immediate surgery may be difficult to plan due to conflicting schedules or procedural logistics, may also benefit from this approach. Patients may also need time to schedule, prepare, and travel to larger medical centers.

Performing surgical resection ranging from 0 to 9 days after robotic assisted nodule marking shows that the intensity of neon-green luminescence from the ICG dye-soaked coil remains constant, rather than fading or dispersing over the pleural surface with time. This approach facilitates patients undergoing a surgical procedure at a later date that will allow appropriate localization and visualization to aid resection by the surgeon. It has the potential to improve the ability to perform successful lung sparing surgery for both primary and secondary lung malignancies.

In Vitro Experiments

In vitro evaluation of ICG retention by fiducial coil markers was conducted.

In an exemplary experiment, a 25 mg ICG vial was reconstituted with 10 cm 3 of sterile water, which is the same dilution that was utilized in vivo. Two types of coils were selected for the experiment, the Cook Medical Tornado 7 mm×3 mm coil with nylon fibers and the Boston Scientific Vortex 18 2 mm×3 mm coil with polyester fibers. The coils were soaked with 0.5 $cm^3$ of diluted ICG by slowly injecting the diluted ICG solution into the coil cartridge. The ICG-infused coils were then set aside for 10 minutes. Prior to implantation into tissue, another 0.5 $cm^3$ of diluted ICG was flushed into the cartridge sheath of the coil.

Freshly harvested and refrigerated beef liver was used in the experiment. The full organs were dissected into large pieces (approximately 10 cm×5 cm). Two small incisions at least 5 cm apart were made with a blade on the liver tissue. Each incision was about 2 cm deep, and the depth was confirmed with a measuring tape scale. One Tornado 7×3 mm ICG impregnated coil and one Vortex 2×3 mm ICG impregnated coil were then inserted with a forceps 2 cm deep into the tissue, at least 5 cm apart. The incisions were then sutured with 2-0 silk and a tape applied on top to identify the site of incision. Five such pieces were created. The pieces were then individually packed in an airtight plastic bag and placed into a container. The container was then placed in a freezer.

The cooled tissue was taken out of the freezer 77 days after the original implantation. The tissue was taken out of the container and thawed at room temperature for about 60 minutes. The tape and sutures were removed from the surface of the tissue. The incision site remained sealed in all of the specimens and the coil was not visible on the surface by visual inspection. The room in which the results were analyzed was darkened, and then the firefly light of an Intuitive Surgical Xi robot was used to illuminate each segment of the tissue individually. All of the coils were illuminated and readily visible.

CONCLUSIONS

A novel method for addressing the problem of surgical localization of lesions or nodules in tissues or organs is described. The disclosed method increases efficiency between a diagnosis and subsequent surgery. The disclosed method may assist surgeons localize small nodules by marking the nodules with a fiducial coil soaked with a fluorescent dye. The fiducial coil may, for example, be used to mark lung nodules and may, for example, be placed at the time of biopsy using a robotic bronchoscopy system. Alternately, non-robotic peripheral navigation platforms may also be used effectively as an adjunct to surgical resection. The dye marks the location of the nodule, making it visible and palpable at the time of surgery. The surgeon can then target cancerous tissue with greater precision. The disclosed method allows a fiducial coil to be placed several days prior to surgery.

Although the examples above illustrate a method of marking lesions in the lungs or alternately in the liver, the disclosed method may be used to mark lesions in other tissues and organs in the body. In addition, although the examples show the use of robotic assisted navigation bronchoscopy (RANB) for placement of a dye-marked fiducial coil in lung tissue, it is contemplated that other techniques may be used for placement of a dye-marked fiducial coil into lung tissue or into other organs or tissues, including but not limited to image guided endoscopic techniques using an endoscope, catheter, or needle and image guided percutaneous techniques using a needle or catheter. Such techniques include, for example, endoscopic ultrasound and CT guided needle placement. Moreover, although the examples illustrate a method of marking lesions using specific coils, it is contemplated that any biocompatible coil suitable for use in the human body, including coils composed of biocompatible metals or alloys, biocompatible polymers, or other biocompatible materials, may be used in the disclosed method. Further, although the examples illustrate the use of a specific biocompatible fluorescent dye, it is contemplated that any biocompatible fluorescent dye suitable for use in the human body may be used in the disclosed method. Also, although the examples illustrate a procedure of soaking the coil in the dye shortly before placing the dye-soaked coil as a marker, it is contemplated that the coil may alternatively be pre-soaked in an appropriate amount of a fluorescent dye and the pre-soaked coil is used in the disclosed method. The shelf-life of pre-soaked coils will depend on the specific dye and the material of which the coil is composed. Finally, although the examples illustrate the use of a coil that is completely soaked in the dye, it is also contemplated that only a portion of the coil is soaked in the dye and such a partially soaked coil is used in the disclosed method.

The previous description of the disclosed embodiments is provided to enable any person skilled in the art to make or use the invention disclosed herein. Although the various inventive aspects are disclosed in the context of certain illustrated embodiments, implementations, and examples, it should be understood by those skilled in the art that the invention extends beyond the specifically disclosed embodiments to other alternative embodiments and/or uses of the invention and obvious modifications and equivalents thereof. In addition, while a number of variations of various inventive aspects have been shown and described in detail, other modifications that are within their scope will be readily apparent to those skilled in the art based upon reviewing this disclosure. It should be also understood that the scope of this disclosure includes the various combinations or sub-combinations of the specific features and aspects of the embodiments disclosed herein, such that the various features, modes of implementation, and aspects of the disclosed subject matter may be combined with or substituted for one another. The generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

All references cited herein are hereby expressly incorporated by reference.

What is claimed is:

1. A method of marking a lesion or nodule within a lung of a mammal for subsequent surgical resection comprising the following steps in order:
   a. soaking a fiducial coil with a solution comprising a fluorescent dye such that the dye penetrates the coil to generate a dye-impregnated fiducial coil; and
   b. placing the dye-impregnated fiducial coil onto or inside the lesion or nodule identified for subsequent surgical resection within the lung of the mammal,
   wherein, following placement of the dye-impregnated fiducial coil onto or inside the lesion or nodule, the dye-impregnated fiducial coil is identifiable using an imaging technique.

2. The method of claim 1, wherein the dye-impregnated fiducial coil is placed onto the lesion or nodule using an image guided endoscopic technique that uses an endoscope, a needle, or a catheter, or using an image guided percutaneous technique that uses a needle or a catheter.

3. The method of claim 2, wherein the dye is indocyanine green.

4. The method of claim 2, wherein a position of the dye-impregnated fiducial coil within the lung is identifiable at least five days after placement of the coil and thereby allows the lesion or nodule to be surgically resected in a lung sparing surgery.

5. The method of claim 1, wherein the dye-impregnated fiducial coil is placed onto the lesion or nodule using a robotic assisted navigation bronchoscopy (RANB) procedure.

6. The method of claim 5, wherein the dye is indocyanine green.

7. The method of claim 1, wherein the dye is indocyanine green.

8. The method of claim 1, wherein the mammal is a human.

9. The method of claim 8, wherein the dye-impregnated fiducial coil is placed onto the lesion or nodule using a robotic assisted navigation bronchoscopy (RANB) procedure.

10. The method of claim 9, wherein the dye is indocyanine green.

11. A method of marking a lesion or nodule within a lung of a mammal for subsequent surgical resection comprising placing a dye-impregnated fiducial coil impregnated with a fluorescent dye onto or inside the lesion or nodule identified for subsequent surgical resection within the lung of the mammal, wherein the dye penetrates the coil,
   wherein, following placement of the dye-impregnated fiducial coil onto or inside the lesion or nodule, the dye-impregnated fiducial coil is identifiable using an imaging technique.

12. The method of claim 11, wherein the dye-impregnated fiducial coil is placed onto the lesion or nodule using an image guided endoscopic technique that uses an endoscope, a needle, or a catheter, or using an image guided percutaneous technique that uses a needle or a catheter.

13. The method of claim 12, wherein the dye is indocyanine green.

14. The method of claim 12, wherein a position of the dye-impregnated fiducial coil within the lung is identifiable at least five days after placement of the coil and thereby allows the lesion or nodule to be surgically resected in a lung sparing surgery.

15. The method of claim 11, wherein the dye-impregnated fiducial coil is placed onto the lesion or nodule using a robotic assisted navigation bronchoscopy (RANB) procedure.

16. The method of claim 15, wherein the dye is indocyanine green.

17. The method of claim 11, wherein the dye is indocyanine green.

18. The method of claim 11, wherein the mammal is a human.

19. The method of claim 18, wherein the dye-impregnated fiducial coil is placed onto the lesion or nodule using a robotic assisted navigation bronchoscopy (RANB) procedure.

20. The method of claim 19, wherein the dye is indocyanine green.

* * * * *